United States Patent
Kluge et al.

(10) Patent No.: US 10,034,955 B2
(45) Date of Patent: Jul. 31, 2018

(54) ACRYLATE ADHESIVE FOR USE ON THE SKIN

(75) Inventors: Thomas Kluge, Vallender (DE); Peter Nissing, Urbach (DE); Patricia Petrick, Oberbaccheim (DE); Mario Schuette, Koblenz (DE)

(73) Assignee: Lohmann GmbH & Co. KG, Neuwied (DE)

( * ) Notice: Subject to any disclaimer, the term of this patent is extended or adjusted under 35 U.S.C. 154(b) by 526 days.

(21) Appl. No.: 13/583,229

(22) PCT Filed: Mar. 29, 2011

(86) PCT No.: PCT/DE2011/000344
§ 371 (c)(1),
(2), (4) Date: Sep. 7, 2012

(87) PCT Pub. No.: WO2011/120507
PCT Pub. Date: Oct. 6, 2011

(65) Prior Publication Data
US 2012/0330211 A1 Dec. 27, 2012

(30) Foreign Application Priority Data
Apr. 3, 2010 (DE) .......... 10 2010 013 799

(51) Int. Cl.
*A61L 24/06* (2006.01)
*A61L 15/58* (2006.01)
*A61L 26/00* (2006.01)

(52) U.S. Cl.
CPC .......... *A61L 15/58* (2013.01); *A61L 24/06* (2013.01); *A61L 26/0014* (2013.01)

(58) Field of Classification Search
CPC ...................................... A61L 24/06
USPC .......................................... 523/118
See application file for complete search history.

(56) References Cited

U.S. PATENT DOCUMENTS

| 4,333,963 | A | * | 6/1982 | Emmons et al. | 427/506 |
| 4,695,608 | A | * | 9/1987 | Engler | C09J 7/021 525/279 |
| 4,879,178 | A | * | 11/1989 | Sun | A61L 15/585 156/331.8 |
| 4,880,683 | A | * | 11/1989 | Stow | C09J 7/00 428/200 |
| 4,921,704 | A | | 5/1990 | Fabo | |
| 5,635,201 | A | | 6/1997 | Fabo | |
| 2003/0073767 | A1 | * | 4/2003 | Husemann et al. | 524/313 |

FOREIGN PATENT DOCUMENTS

| EP | 0 099 748 B1 | 2/1984 | |
| EP | 0 435 199 B1 | 7/1991 | |
| EP | 0 891 782 B1 | 1/1999 | |
| EP | 1 357 140 A1 | 10/2003 | |
| GB | 1 280 631 A | 7/1972 | |
| WO | WO 91/14461 A1 | 10/1991 | |
| WO | WO 9114461 A1 * | 10/1991 | A61L 15/06 |
| WO | WO 98/03208 A1 | 1/1998 | |

* cited by examiner

*Primary Examiner* — Michael Pepitone
(74) *Attorney, Agent, or Firm* — ProPat, L.L.C.

(57) ABSTRACT

The invention relates to the production of a pressure-sensitive adhesive composition polymerized entirely from acrylate-based monomers in a layer thickness of about 250 μm and to the use thereof for adhesion to human skin. The adhesive films thus produced adhere reliably to human skin, have high water-vapor permeability despite the layer thickness, with the result that, for example, wound healing is promoted, and even after a relatively long wearing period can be removed from the skin again without leaving a residue and without damaging the skin.

12 Claims, No Drawings

ACRYLATE ADHESIVE FOR USE ON THE SKIN

CROSS-REFERENCE TO RELATED APPLICATIONS

This application is being filed under 35 USC § 371 as a National Stage Application of pending International Application No. PCT/DE2011/000344 filed Mar. 29, 2011, which claims priority to German Patent Application No. 10 2010 013 799.5, filed Apr. 3, 2010. Both International Application No. PCT/DE2011/000344 and German Patent Application No. 10 2010 013 799.5 are hereby incorporated by reference herein in their entirety.

FIELD OF THE INVENTION

The present invention relates to the preparation of a pressure-sensitive adhesive and to the use thereof for bonding to the human skin. The monomer constituents of the polymeric, pressure-sensitive adhesive that are used in accordance with the invention consist 100% of acrylate-based monomers. The adhesive films produced therefrom, in a layer thickness of approximately 250 μm, have reliable adhesion to the human skin, possess high water vapor permeability in spite of the layer thickness, thereby promoting wound healing, for example, and even after a prolonged wearing period can be detached from the skin again without residue and without damage to the skin.

BACKGROUND OF THE INVENTION

There are a multiplicity of applications in the medical sector that require affixment to the human skin by means of suitable pressure-sensitive adhesives. In view of the sensitivity of these applications, specific pressure-sensitive adhesives are employed here. These adhesives are required to meet the inherently contradictory requirements on the one hand of reliable bonding to the skin in all its variants, varying depending on the age and health condition of the patient, during application, and on the other of very substantially painless and residue-free detachment after application. Furthermore, they must not contain any substances which are sensitizing or are harmful to the skin in any other respect. Acrylate-based pressure-sensitive adhesives represent a class of adhesives frequently used in this sector. The advantage of these materials lies in their excellent adhesion, the high compatibility of the ingredients with the human skin, the low tendency toward sensitization, and the very good sterilization stability and aging resistance.

Thus EP 0 099 748 B1 describes a wound dressing based on a pressure-sensitive polyacrylate adhesive with high water vapor permeability. A disadvantage is the tendency on the part of the acrylate-based pressure-sensitive adhesives to increase bond adhesion with increasing wearing period, owing to increasing enhancement of the wetting of the skin by the pressure-sensitive adhesive. This is especially disadvantageous when the pressure-sensitively adhesive product is required, for therapeutic reasons, to spend a long time on the skin, after which it has to be removed from the skin again mechanically. In this case, in practice, there are frequent instances of injury to the skin as a result of the extraction of skin cells. In order to counter this effect, high molecular mass, pressure-sensitive acrylate adhesives are used in conjunction with plasticizing additives as adhesives for wound dressings. A solution of this kind is described, for example, in patents EP 0 891 782 B1 whose United States equivalent is U.S. Pat. No. 6,231,883 and EP 0 435 199 B1. The use of the plasticizing ingredients, in conjunction with the high molecular mass polymer matrix, produces reliable adhesion to the human skin. A disadvantageous effect here, however, is the migration tendency of the plasticizing components. This results, as a consequence of the mixing of two components having different adhesion behaviors, to nonuniform peeling behavior from the skin.

For this reason, the present state of the art is to use silicone gel adhesives for such applications. The advantage of these adhesives is that even after a long wearing period, they can be peeled from the skin easily and without skin damage. Thus U.S. Pat. No. 4,921,704 describes a wound dressing for exuding wounds, consisting of a porous adhesive layer based on a silicone gel adhesive, and an external absorption layer. U.S. Pat. No. 5,635,201 describes the production of a wound dressing by application of a pressure-sensitive silicone gel adhesive layer to a porous substrate with retention of the porosity. Disadvantages of these solutions, as well as the elevated costs, are the lower bond strength as compared with acrylate-based pressure-sensitive adhesives, and the very low water vapor permeability. A consequence of this is that pressure-sensitive adhesive products based on silicone gel adhesives cannot be applied over their full area to the human skin, since otherwise, as a result of the absent breathability of these adhesive films, macerations may occur to the skin, especially in the course of prolonged wearing periods. From a technological standpoint, production of the interrupted layers of adhesive with these pressure-sensitive adhesives is very complicated, and has the effect of further impairing the bond strength in comparison to acrylate-based pressure-sensitive adhesives.

SUMMARY OF ADVANTAGEOUS EMBODIMENTS OF THE INVENTION

Against this background, an object of the present invention was to provide acrylate-based pressure-sensitive adhesives which have good bond strength to the human skin, possess high water vapor permeability even at relatively high layer thicknesses, exhibit good biocompatibility, and can be peeled from the human skin without damage even after prolonged wearing periods.

DETAILED DESCRIPTION OF ADVANTAGEOUS EMBODIMENTS OF THE INVENTION

It has been possible to achieve this object, in a way which is surprising and, for the skilled person, unforeseeable, by means of the pressure-sensitive adhesives of the invention.

These pressure-sensitive adhesives of the invention can be prepared by polymerization of the monomers in the presence of a radical initiator. This procedure may be performed either in a suitable solvent or else solventlessly. The solventless embodiment is particularly preferred here.

Monomers which can be used for preparing the pressure-sensitive adhesives of the invention include ethylenically unsaturated compounds such as, for example, (meth)acrylates. (Meth)acrylates in the sense of the present invention are esterification products of acrylic acid or methacrylic acid with monohydric alcohols. The (meth)acrylates are preferably esterification products of acrylic acid or meth(acrylic acid) with monohydric or polyhydric alcohols comprising 1 to 20 C atoms, preferably 6 to 10 C atoms, where the alcohol function may be present as a primary, secondary, tertiary or cyclic radical. The meth(acrylates) are selected more particularly from the group consisting of methyl (meth)acrylate, ethyl (meth) acrylate, butyl (meth)acrylate, hexyl (meth) acrylate, isooctyl (meth)acrylate, 2-ethylhexyl (meth)acrylate, isodecyl (meth)acrylate, isobornyl (meth)acrylate, ethoxy(ethoxy)ethyl (meth)acrylate, phenoxyethyl acrylate, hexanediol acrylate, hexanediol diacrylate, hydroxyalkyl (meth)acrylate with an alkyl radical of preferably 1-20 C atoms, polyethylene glycol (meth)acrylate with 5-10 ethylene oxide units, (meth)acrylic acid, and glycidyl (meth)acrylate.

It is also possible to use mixtures of the abovementioned compounds.

As initiators for the radical polymerization of the monomers it is possible to use not only water-soluble but also oil-soluble compounds which, by thermal, chemical or electromagnetic activation, form reactive radicals; more particularly peroxodisulfates and organic hydroperoxides, such as potassium peroxo disulfate, sodium peroxodisulfate, cumene hydroperoxide, azobisisobutyronitrile, butyl hydroperoxide, m-chloroperbenzoic acid, benzophenone, bis(2,6-dimethoxybenzoyl)-2,4,4-trimethylpentylphosphine oxide, 2,4,6-trimethylbenzophenone, 2-hydroxy-2-methyl-1-phenyl-1-propanone, 2,4,6 trimethylbenzoyldiphenylposhine oxide, 1-[4-(2-hydroxyethoxy)phenyl]-2-hydroxy-2-methyl-1-propanone, and 1-hydroxycyclohexyl phenyl ketone, and also mixtures of these initiators.

For the polymerization of the monomer components it is possible to use not only inorganic but also organic reducing agents, preferably alkali metal salts of sulfurous or disulfurous acid such as sodium sulfite, sodium disulfite or sodium hydrogensulfite, hydroxymethanesulfinic acid and its salts, and also primary and secondary amines, such as triethylamine and diethylenetetramine, and mixtures of the abovementioned compounds.

The initiators and reducing agents are used preferably in a fraction of 0.1-5% by weight, more preferably in a fraction of 0.5-3% by weight, based on the amount of the monomer components.

The polymerization of the pressure-sensitive adhesives of the invention may be triggered not only by temperature but also by actinic radiation. Particularly preferred is the initiation of the polymerization reaction by UV radiation.

The polymerization of the pressure-sensitive adhesives of the invention may be carried out alternatively in a solvent-based, water-based or solventless process. These processes are known to the skilled person.

The present invention is further directed to the use of the polymers of the invention for bonding to human skin, as for example in the sector of wound management, of transdermal therapeutic systems or of ostomy management.

In order to adjust the viscoelastic properties it is possible to add polyfunctional monomers to the monomer mixture. Examples of such polyfunctional compounds include tripropylene glycol diacrylate, trimethylolpropane triacrylate and pentaerythritol (meth)acrylate. The crosslinker fraction in the pressure-sensitive adhesives of the invention is 0.01% to 5.0%, preferably from 0.07% to 3.0%, and more preferably from 0.15% to 1.8%.

As liner materials for the adhesive it is possible to use the sheet materials known to the skilled person which have, relative to the pressure-sensitive adhesives of the invention, a level of release that allows reliable storage and processing in roll form and in diecut form. Such materials include, for example, siliconized films based on polyester, polyethylene, and polypropylene, and also siliconized papers.

The examples below illustrate the present invention, without restricting it to the working examples.

EXAMPLES 1-5 PREPARATION OF THE INVENTIVE POLYMERS AND PRODUCTION OF THE ADHESIVE FILMS

For each of examples 1-5, first of all, a three-neck flask with stirrer, reflux condenser, and dropping funnel is charged with a monomer mixture consisting of 50 pbw of polyethylene glycol methacrylate 550 and 50 pbw of 2-ethylhexyl acrylate together with 3 pbw of the initiator 2,4,6-trimethylbenzophenone. The mixture is then irradiated with a UV lamp over a time of 10 minutes. The mixture is subsequently discharged through a 50 µm filter. The conversion rate is 36%.

Example 1

800 pbw of the polymer prepared first and described are admixed with 6 pbw of tripropylene glycol diacrylate and 10 pbw of the initiator 2,4,6-trimethyl benzophenone. Using a laboratory doctor knife, the mixture is applied with a layer thickness of 250 µm and irradiated with a UV lamp over a time of 30 seconds. The residual monomer content of the resultant adhesive films is 120 ppm.

Example 2

800 pbw of the polymer prepared first and described are admixed with 4 pbw of tripropylene glycol diacrylate and 10 pbw of the initiator 2,4,6-trimethyl benzophenone. Using a laboratory doctor knife, the mixture is applied with a layer thickness of 250 µm and irradiated with a UV lamp over a time of 30 seconds. The residual monomer content of the resultant adhesive films is 150 ppm.

Example 3

800 pbw of the polymer prepared first and described are admixed with 2 pbw of tripropylene glycol diacrylate and 10 pbw of the initiator 2,4,6-trimethyl benzophenone. Using a laboratory doctor knife, the mixture is applied with a layer thickness of 250 µm and irradiated with a UV lamp over a time of 30 seconds. The residual monomer content of the resultant adhesive films is 170 ppm.

Example 4

800 pbw of the polymer prepared first and described are admixed with 2 pbw of tripropylene glycol diacrylate and 10 pbw of the initiator azobisisobutyronitrile. Using a laboratory doctor knife, the mixture is applied with a layer thickness of 250 µm and irradiated with a NIR lamp ("Lambda Technologies") over a time of 90 seconds. The residual monomer content of the resultant adhesive films is 200 ppm.

Example 5

A three-necked flask with stirrer, reflux condenser, and dropping funnel is charged with 460 pbw of ethyl acetate and is heated to boiling with stirring. When the boiling point is reached, 30% of a monomer mixture consisting of 2 pbw of acrylic acid, 25 pbw of ethylhexyl acrylate, and 25 pbw of polyethylene glycol methacrylate, and 30% of the initiator solution consisting of 0.3 pbw of azobisisobutyronitrile in 50 pbw of ethyl acetate, are introduced. Thereafter, in parallel, the remaining 70% of the monomer mixture and of the initiator solution are metered in over a time of 60 minutes. Subsequently, again, a solution of 0.1 pbw of azobisisobutyronitrile in 90 pbw of ethyl acetate is added and the batch is stirred for 120 minutes, cooled, and discharged through a 50 μm filter. The polymer has an average molecular weight of 780 000. The polydispersity is 10.1. The residual monomer content is 200 ppm. By means of a laboratory doctor knife, the mixture is applied with a layer thickness of 125 μm. In order to obtain the final layer thickness of 250 μm, two of these films are laminated together at room temperature with a pressure of 3 bar.

Adhesive Film Testing

The water vapor permeability was determined on the one hand in accordance with DIN EN 13726-2 at a temperature of 37° C. and an atmospheric humidity of 18%, and on the other hand in accordance with ASTM E 96 by the upright cup method at a temperature of 23° C. and an atmospheric humidity of 50%. For the evaluation of the low-trauma characteristics, a wearing test was carried out over a period of 24 h, and was evaluated according to the following qualitative criteria:

1—no residues of adhesive on the skin, no detachment of skin cells on peeling
2—no residues of adhesive on the skin, slight detachment of skin cells on peeling (<5% of the bonding area)
3—slight residues of adhesive (<5% of the bonding area) on the skin, slight detachment of skin cells on peeling
4—slight residues of adhesive on the skin, severe detachment of skin cells on peeling
5—severe residues of adhesive on the skin, severe detachment of skin cells on peeling As part of the wearing test, an evaluation was also made of reliable hold on the human skin. In this case the evaluation scale used as a basis was as follows:

1—very good adhesion, no detachment under load
2—good adhesion, occasional detachment at the corners
3—poor adhesion, severe detachment at corners
4—very poor adhesion, occasional complete detachment
5—no adhesion, frequent complete detachment With the adhesive bonding agents prepared in the stated examples, in accordance with ASTM E 96 by the upright cup method at a temperature of 23° C. and an atmospheric humidity of 50%, the results obtained were as follows:

|  | Unit | Example 1 | Example 2 | Example 3 | Example 4 | Example 5 |
|---|---|---|---|---|---|---|
| Water vapor permeability | g/m² 24 h | 1280 | 1390 | 1530 | 1330 | 1070 |
| Wearing test | 1-5 | 1 | 1-2 | 2 | 1-2 | 2 |
| Adhesion to the skin | 1-5 | 1-2 | 1 | 1 | 2 | 2 |

In accordance with DIN EN 13726-2, the wearing test and the adhesion to the skin at a temperature of 37° C. and an atmospheric humidity of 18% gave similar results; in all cases here, the water vapor permeability was between 1000 and 1200 g/m² over 24 h.

The values show that for all of the inventive adhesive films, both a high water vapor permeability of >1000 g/m² over 24 h and also minimal or no damage to the epidermis were achieved. In the wearing test, all of the samples exhibited reliable adhesion to the human skin.

The invention claimed is:

1. A polymeric, pressure-sensitive adhesive consisting of radical initiator(s) and acrylate-based monomers that consist of polyethylene glycol methacrylate and esterification products of acrylic acid or methacrylic acid with monohydric or polyhydric alcohols having 6 to 20 C atoms (iii) optional additional polyfunctional monomers adjusting viscoelastic properties selected from tripropylene diacrylate, trimethylolpropane triacrylate and pentaerythritol (meth)acrylate, wherein at a layer thickness of 250 μm the adhesive has a water vapor permeability, as measured to ASTM E 96 by the upright cup method at a temperature of 23° C. and an atmospheric humidity of 50% and to DIN EN 13726-2 at a temperature of 37° C. and an atmospheric humidity of 18%, of at least 1000 g/m² over 24 h, wherein said adhesive is prepared by polymerization of said monomers in the presence of radical initiator(s) selected from a group consisting of peroxodisulfates and organic hydroperoxides,
said adhesive adheres to human skin at a temperature of 37° C. and atmospheric humidity of 18%.

2. The polymeric, pressure-sensitive adhesive of claim 1, wherein said adhesive is prepared by UV polymerization.

3. The polymeric, pressure-sensitive adhesive of claim 1, wherein said adhesive is prepared by thermal polymerization.

4. The polymeric, pressure-sensitive adhesive of claim 1, wherein said adhesive is prepared by polymerization without using organic solvents.

5. The polymeric, pressure-sensitive adhesive of claim 1, wherein said adhesive is prepared by solvent-based polymerization.

6. The polymeric, pressure-sensitive adhesive of claim 1 bonded to human skin.

7. The polymeric, pressure-sensitive adhesive of claim 6, wherein even after a wearing time of up to 24 h, said adhesive can be detached from the human skin without residues of adhesive and with detachment of skin cells limited to not more than 5% of the bonding area.

8. The polymeric, pressure-sensitive adhesive of claim 1, wherein the polyfunctional monomers are present in an amount ranging from 0.01 to 5.0%.

9. A polymeric, pressure-sensitive adhesive, consisting of radical initiator(s) and acrylate-based monomers that consist of esterification products of (i) acrylic acid or methacrylic acid with (ii) monohydric or polyhydric alcohols in which the monohydric or polyhydric alcohols have 1 to 20 C atoms and (iii) optional additional polyfunctional monomers adjusting viscoelastic properties selected from tripropylene diacrylate, trimethylolpropane triacrylate and pentaerythritol (meth)acrylate, wherein at a layer thickness of 250 μm the adhesive has a water vapor permeability, as measured to ASTM E 96 by the upright cup method at a temperature of 23° C. and an atmospheric humidity of 50% and to DIN EN 13726-2 at a temperature of 37° C. and an atmospheric humidity of 18%, of at least 1000 g/m² over 24 h, wherein polyethylene glycol (meth)acrylate with 5 to 10 ethylene oxide units is an acrylate-based monomer.

10. A polymeric, pressure-sensitive adhesive, consisting of radical initiator(s) and acrylate-based monomers that consist of esterification products of (i) acrylic acid or methacrylic acid with (ii) monohydric of polyhydric alcohols in which the monohydric or polyhydric alcohols have 1 to 20 C atoms and (iii) optional additional polyfunctional monomers adjusting viscoelastic properties selected from tripropylene glycol diacrylate, trimethylolpropane triacrylate and pentaerythritol (meth)acrylate, wherein at a layer thickness of 250 μm the adhesive has a water vapor permeability, as measured to ASTM E 96 by the upright cup method at a temperature of 23° C. and an atmospheric humidity of 50% and to DIN EN 13726-2 at a temperature of 37° C. and an atmospheric humidity of 18%, of at least 1000 g/m² over 24 h, wherein the acrylate-based monomers consist of polyethylene glycol methacrylate and ethylhexyl acrylate and the additional polyfunctional monomer is tripropylene glycol diacrylate.

11. The polymeric, pressure-sensitive adhesive of claim 10, wherein the polyethylene glycol methacrylate and ethylhexyl acrylate are present in equal proportion.

12. A polymeric, pressure-sensitive adhesive of claim 9, wherein said radical initiator(s) is selected from the group consisting of potassium peroxodisulfate, sodium peroxodisulfate, cumene hydroperoxide, azobisisobutyronitrile, butyl hydroperoxide, m-chloroperbenzoic acid, benzophenone, bis(2,6-dimethoxybenzoyl)-2,4,4-trimethylpentylphosphine oxide, 2,4,6-trimethylbenzophenone, 2-hydroxy-2-methyl-1-phenyl-1-propanone, 2,4,6 trimethylbenzoyldiphenylphosphine oxide, 1-[4-(2-hydroxyethoxy)phenyl]-2-hydroxy-2-methyl-1-propanone, and 1-hydroxycyclohexyl phenyl ketone, and mixtures of thereof.

* * * * *

UNITED STATES PATENT AND TRADEMARK OFFICE
CERTIFICATE OF CORRECTION

PATENT NO. : 10,034,955 B2
APPLICATION NO. : 13/583229
DATED : July 31, 2018
INVENTOR(S) : Kluge et al.

Page 1 of 1

It is certified that error appears in the above-identified patent and that said Letters Patent is hereby corrected as shown below:

On the Title Page

Item (57) Abstract
Line 2, delete "polymerized" insert --polymerised--

In the Claims

Column 6
Claim 1, Line 1, delete "(iii)" insert --and--
Claim 1, Line 3, delete "tripropylene diacrylate" insert --tripropylene glycol diacrylate--
Claim 9, Line 46-47, delete "tripropylene diacrylate" insert --tripropylene glycol diacrylate--

Column 7
Claim 12, Line 21, delete "of"

Signed and Sealed this
Sixth Day of November, 2018

Andrei Iancu
*Director of the United States Patent and Trademark Office*